United States Patent [19]

Lindstrom et al.

[11] Patent Number: 5,366,964

[45] Date of Patent: Nov. 22, 1994

[54] VISCOELASTIC SOLUTION

[76] Inventors: Richard L. Lindstrom, 20050 Lakeview Ave., Excelsior, Minn. 55331; Debra Skelnik, P.O. Box 758, Rte. 1, Cambridge, Minn. 55008

[21] Appl. No.: 434,305

[22] Filed: Nov. 13, 1989

Related U.S. Application Data

[62] Division of Ser. No. 284,533, Dec. 15, 1988, Pat. No. 5,013,714.

[51] Int. Cl.$^5$ ............................................. A61K 31/715
[52] U.S. Cl. ...................................... 514/57; 514/54; 514/59; 514/912
[58] Field of Search .................. 514/54, 57, 59, 23, 514/2, 12, 912, 3; 530/324

[56] References Cited

U.S. PATENT DOCUMENTS 4,713,375  12/1987  Lindstrom et al. ................... 514/54
4,886,786  12/1989  Lindstrom et al. ................... 514/54
5,013,714   5/1991  Lindstrom et al. ................... 514/57

OTHER PUBLICATIONS

Couch et al., "Mitotic Activity of Corneal Endothelial Cells in Organ Culture with Recombinant Human Epidermal Growth Factor", Ophthalmology, Jan., 1987, vol. 94, No. 1, pp. 1–4.

*Primary Examiner*—Johnnie R. Brown
*Assistant Examiner*—Everett White
*Attorney, Agent, or Firm*—Hugh D. Jaeger

[57] ABSTRACT

A viscoelastic solution including a buffered solution, 0.01–10% chondroitin sulfate, 0.01–10% hydroxypropyl methylcellulose, and 0.01–10% sodium hyaluronate, pH adjusted to 6.0–8.0 at a osmolarity between 200–400 mOsmol/L. The buffered solution can be HEPES buffered minimal essential medium (MEM), phosphate buffered saline (PBS), or buffered balanced salt solution. A cell growth factor or cell growth supplement can also be included in the solution.

1 Claim, 2 Drawing Sheets

VISCOELASTIC SOLUTION

CROSS REFERENCES TO CO-PENDING APPLICATIONS

This application is a divisional of U.S. patent application Ser. No. 07/284,533, filed Dec. 15, 1988, entitled "Viscoelastic Solution" to the same inventors, now U.S. Pat. No. 5,013,714.

BACKGROUND OF THE INVENTION

1. Field of the Invention

The present invention pertains to a viscoelastic solution for ocular and surgical applications. The viscoelastic solution is used during surgery to protect cells from mechanical trauma, to maintain or create tissue spaces, to ensure separation and lubrication of tissue surfaces, to permit the manipulation of tissues without mechanical damage, and to provide cell growth factors, cell supplements and/or basement membrane components that support wound healing. The present invention more particularly pertains to a viscoelastic solution utilizing three components, including chondroitin sulfate, hydroxypropyl methylcellulose and sodium hyaluronate.

2. Description of the Prior Art

There have been numerous prior art solutions such as Ultrapure Hyaluronic Acid and Use Thereof as described in U.S. Pat. No. 4,141,973 to Balazs. Another such viscoelastic solution is described in U.S. Pat. No. 4,713,375 to Lindstrom and Skelnik, issued on Dec. 15, 1987.

The present invention overcomes the disadvantages of the prior art by providing a viscoelastic solution for surgical use and also a viscoelastic solution with growth factors for surgical use.

SUMMARY OF THE INVENTION

The general purpose of the present invention is a viscoelastic solution which provides a buffered pH neutral solution as a base, and includes the components of the combination of chondroitin sulfate, hydroxypropyl methylcellulose and sodium hyaluronate. The viscoelastic solution can also include a cell growth factor, cell growth supplement or basement membrane component.

Growth factors (GF), which may be employed in the compositions and methods of this invention include polypeptides or other substances possessing the ability to enhance corneal wound healing, reduce or eliminate the normal progressive loss of endothelial cells, and/or stimulate the mitotic potential of these ocular tissues when applied thereto. In a wider use of surgical application, growth factors can be used to induce tissue specific wound healing. For example, epidermal growth factor (EGF), fibroblastic growth factor (FGF), platelet-derived growth factor (PDGF), transforming growth factor alpha (TGF-$\alpha$), transforming growth factor beta (TGF-$\beta$), insulin-like growth factor I (IGF-I), insulin like growth factor II (IGF-II), and insulin are all agents which possess the ability to stimulate the division or maturation of certain cell types. Each of these polypeptides enhance, to varying degrees, activities in cell types other than those from which they are derived.

In accordance with the present invention, the viscoelastic solutions may contain one or more growth factors, such as epidermal growth factor (EGF), insulin-like growth factor I (IGF-I), fibroblastic growth factor (FGF), transforming growth factor alpha (TGF-$\alpha$), transforming growth factor beta (TGF-$\beta$), platelet derived growth factor (PDGF) and insulin and the like provide increased cell viability and potentiate the mitotic activity of target cells that come into contact with growth factors. Specifically in corneal tissue, growth factors can bind to both the corneal epithelium, endothelium or other tissues after coming into contact with the growth-factor containing viscoelastic solution. The effects of the viscoelastic solution contain a growth factor(s) which is not limited to human ocular cells.

Many cells are terminally differentiated and are unable to undergo mitosis. However, there are many differentiated cells that retain the ability to return to the cell cycle if provided with an appropriate mitogenic signal, usually in the form of specific growth factor. Cell growth is carefully regulated to ensure that sufficient cells are produced during development and that cells reenter the cell cycle at appropriate times commensurate with requirements for new cells and for body repair and other functions. As a surgical viscoelastic solution containing a growth factor or growth supplement, this solution would be in direct contact with cells undergoing wound healing.

Growth factors do require time to act. Although growth factors can switch on the transcription of certain genes within minutes, such short stimulations are usually not adequate to induce DNA synthesis. The growth factor must act for several hours, which presumably means that it must be capable of activating the signal pathway for a protracted period. This need for a prolonged stimulus could possibly be the basis for the synergistic interactions that exist between various growth factors. When growth factors combine with cell surface receptors, they entrain a sequence of events that gradually commits the cell to enter DNA synthesis.

The combination of chondroitin sulfate, hydroxypropyl methylcellulose and sodium hyaluronate provide a significant aspect and feature of the present invention, which provides better viscosity including the viscous and lubricating properties of the hydroxypropyl methylcellulose, chondroitin sulfate, and sodium hyaluronate. The combination of these three components also provide cell protection and cell coating during surgery. The solution provides maintenance of the tissue space, the chondroitin sulfate and hydroxypropyl methylcellulose lubricates the tissue while the sodium hyaluronate provides tissue manipulation. The biocompatible properties of these three components allows the components to remain in the body cavity or would site, and promote wound healing. Therefore, the extended release of one or more growth factors over time may provide the continuous stimulation needed to commit cells to undergo mitosis.

The application of recombinant DNA technology to the production of growth factor proteins has now made it possible to formulate chemically defined growth factor supplemented viscoelastic solutions for comparative evaluation of tissue enhancement. While recombinant growth factors are preferred, growth factors derived from natural biological sources are useful in the present invention.

Epidermal growth factor (EGF), acidic and basic fibroblastic growth factor (FGF), transforming growth factor alpha (TGF-$\alpha$) and transforming growth factor beta (TGF-$\beta$), platelet-derived growth factor (PDGF), insulin, and insulin-like growth factor I (IGF-I) are known proteins whose properties and biological activities have been well characterized. These peptide growth factors are described for example in the recent review articles by Krisis et al., *Biotechnology*, February, 1985, pp. 135-140 and in *Hormonal Proteins and Peptides*, Ed. by Choh Hao Li, Vol. 12, "Growth Factors" Academic Press (1984).

EGF is a low molecular weight protein (6040 mw) previously isolated from mouse salivary glands according to the method fo Savage and Cohen, J. Biol. Chem., 1972:257:7609-11. European Patent Office publication number EP 177,915 teaches the production of recombinant human EGF by *E.coli* transformed with a synthetic gene.

FGF has been isolated and purified from natural sources (R. R. Lobb, J. W. Harper, J. W. Fatt, Purification of Heparin-Binding growth factors, *Anal. Biochem.* 154:1-14, 1986). Production of recombinant FGF is described in published European Patent Application EP 248,819.

EP 200,341 describes the production of TGF-β by transforming a eukaryotic cell with a vector.

A process for obtaining TGF- is described in J. E. DeLarco and G. E. Todaro, Growth Factors from Murine Carcoma Virus-Transformed Cells, *Pro. Natl. Acad. Sci.* USA, 75:4001-4005, 1978.

EP 219,814 teaches the production of recombinant human IGF-I. E. Rinderkneot and R. E. Humbel teach the production of IGF-I from natural sources in Polypeptides with Non-Suppressible Insulin-Like and Cell-Growth Promoting Activities in Human Serum; Isolation, Chemical Characterization and Some Biological Properties of Forms I and II, *Proc. Natl. Acad. Sci* USA, 73; 2365-2369, 1976.

As used herein, unless otherwise indicated, the term "growth factor" is intended to include the above described peptide growth factors, as well as biologically active fragments and derivatives thereof, including precursors that may be proteolytically processed into biologically active growth factors in human cells.

Other significant aspects and features of the present invention is a viscoelastic solution for use in all surgical applications, including, but not limited to ophthalmology, orthopedics, dermatology, gastroenterology, gynecology, nephrology, neurology, obstetrics, onocology, otolaryngology, pediatrics, pharmacology, rheumatology, urology, and any other surgical or non-surgical application.

Having thus described the embodiments of the present invention, it is a principal object hereof to provide a viscoelastic solution with three components.

One object of the present invention is a viscoelastic solution with three components or a viscoelastic solution with three components supplemented with one or more of the following cell growth factors, cell growth supplements, and/or basement membrane components.

Another object of the present invention is a viscoelastic solution for any surgical use internal or external to the human body.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
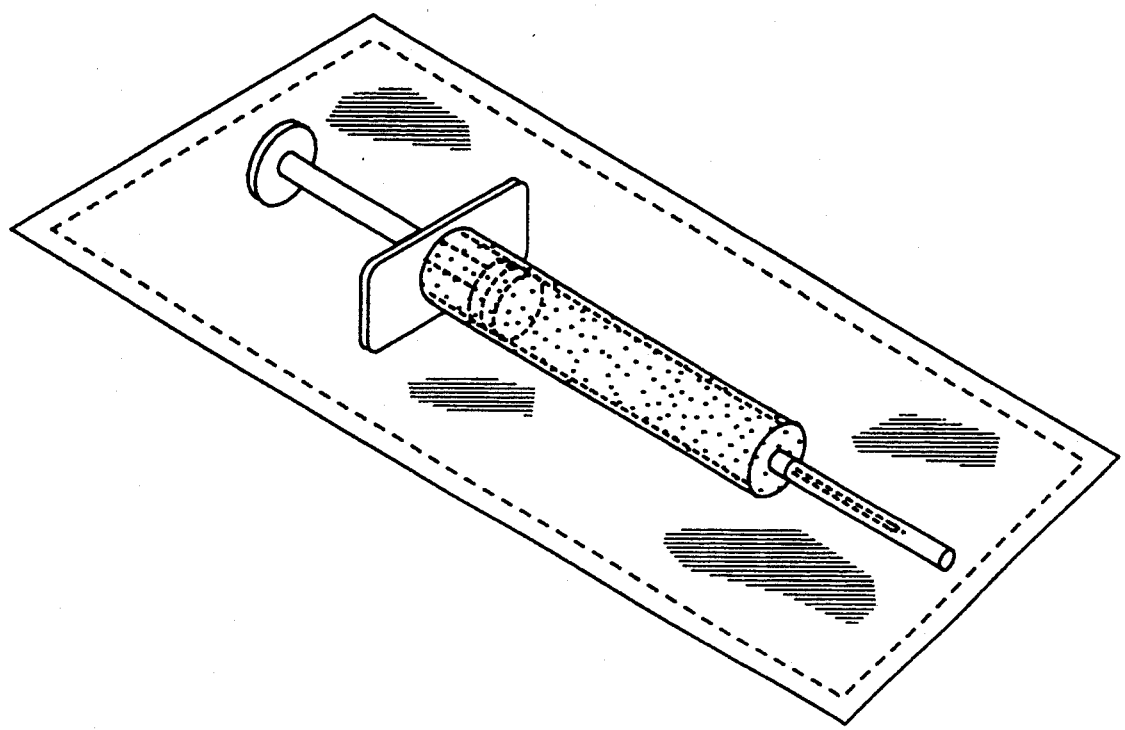
FIG. 1 illustrates a perspective view of a finite quantity of viscoelastic solution contained in a syringe and in a sterilized package; and, FIG. 2 shows the dose response curve of hEGF in a chondroitin sulfate, hydroxypropyl methylcellulose, and sodium hyaluronate based viscoelastic to stimulate $^3$H-thymidine incorporation into the DNA of human corneal endothelial cells in vitro.
Figure 2:
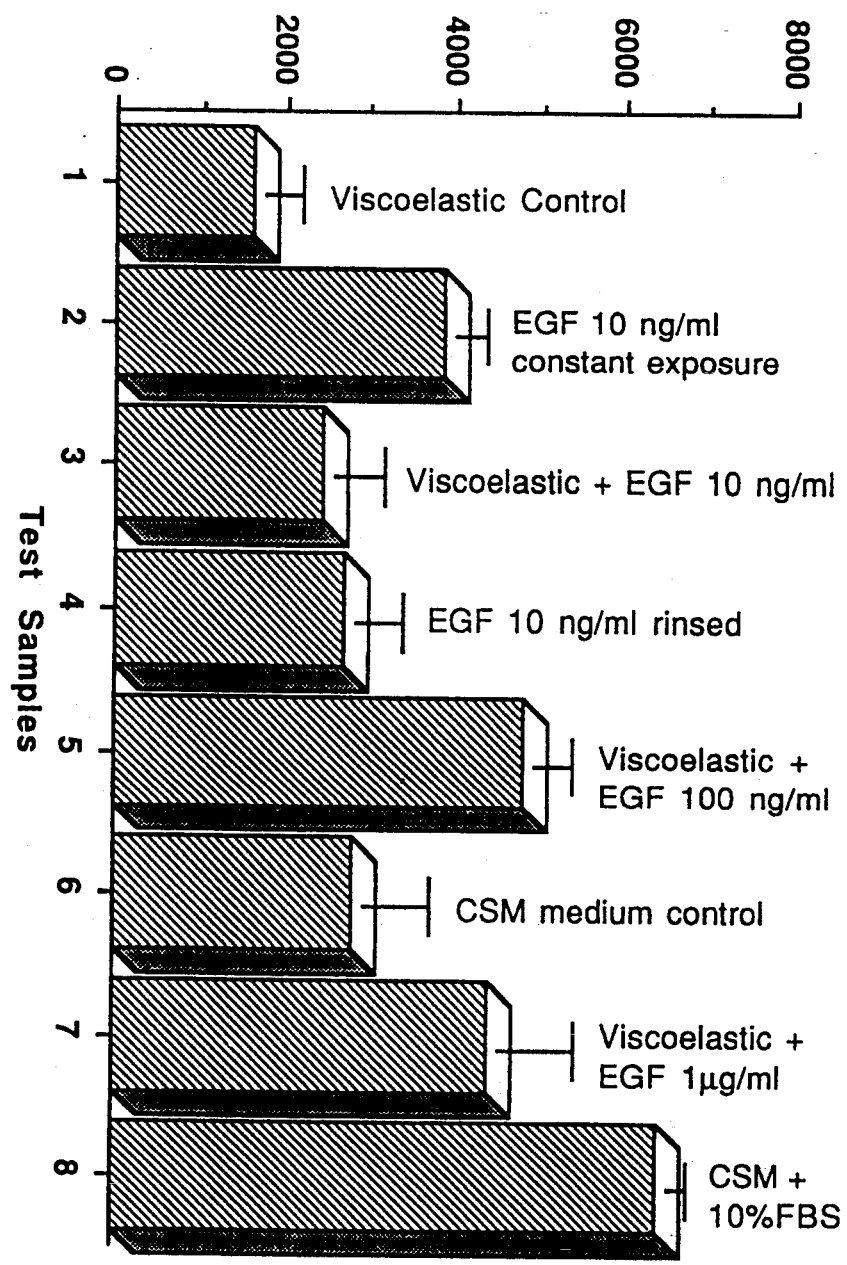

The viscoelastic solution includes a buffered solution, 0.01-10% hydroxypropyl methylcellulose and 0.01-10% chondroitin sulfate, and 0.01-10% sodium hyaluronate, pH adjusted to 6.0-8.0 and having an osmolality of 200-400 mOsmol/L. The buffered solution can be selected from HEPES buffered minimum essential medium (MEM), phosphate buffered saline (PBS), buffered balanced salt solution (BSS), or tissue culture medium 199. The hydroxypropyl methylcellulose can be substituted with either carboxypropyl methylcellulose, a cellulose gum, dextran or dextran sulfate. Preferably, the hydroxypropyl methylcellulose is present at a concentration of 0.01-10% while the chondroitin sulfate can be present at a concentration of 0.01-10% by volume.

The solution hyaluronate can be present at a concentration of 0.01-10% by volume. The solution can be specifically introduced onto the eye during surgery to protect cells from trauma, to provide lubrication during the procedure, and to promote ocular wound healing.

In a wider application, the solution can be introduced into the wound site, to protect the cells from surgical trauma, to provide lubrication during the procedure, and to promote cellular wound healing.

Cell growth factors or growth supplements which can be used in the viscoelastic solution are:

1. Fibroblastic growth factor (FGF), a single chain polypeptide, isolated and purified from the pituitary, human (hFGF) fibronectin or bovine fibronectin (bFGF), in either the acidic or basic forms. The molecular weight range is 14,000 to 16,000. This factor has been demonstrated mitogenic in vitro to a wide variety of cells comprising mesoderm and neuroectoderm tissue.

This also includes synthetic formulated FGF basic peptides consisting of: (1–24) Pro-Ala-Leu-Pro-Glu-Asp-Gly-Gly-Ser-Gly-A-Phe-Pro-Pro-Gly-His-Phe-Lys-Asp-Pro-Lys-Arg-Leu-Try and synthetic formulated FGF acidic peptides consisting of: (1–11) Phen-Asn-Leu-Pro-Leu-Gly-Ans-Tyr-Lys-Lys-Pro. The fibroblastic growth factor can be used at concentrations of 0.1 ng/ml–100 mg/ml.

2. Endothelial Cell Growth Factor (ECGF), prepared from the hypothalamus as a lyophyilized extract. This growth supplement has been demonstrated mitogenic in vitro to a wide variety of endothelial cells; i.e., human corneal endothelial cells, human umbilical vein endothelial cells, and mouse Balb/c fibroblasts. The Endothelial Cell Growth Factor can be used at concentrations of 0.1 ng/ml to 500 mg/ml.

3. Uragastrone or Epidermal Growth Factor (EGF), a single chained polypeptide, is composed of 53 amino acids, containing 3 disulfide bonds and has been isolated from mouse submaxillary glands (mEGF) and human urine. This growth factor has been demonstrated to be mitogenic in vitro for a wide variety of cells of ectodermal and mesodermal origin.

This includes both naturally occurring and synthetic human and mouse EGF: Asn-Ser-Tyr-Pro-Gly-Cys-Pro-Ser-Ser-Try-Asp-Gly-Tyr-Cys-Leu-Asn-Gly-Gly-Val-Cys-Met-His-Ile-Glu-Ser-Leu-Asp-Ser-Tyr-Thr-Cys-Asn-Cys-Val-Ile-Gly-Try-Ser-Gly-Asp-Arg-Cys-Gln-Thr- Arg-Asp-Leu-Arg-Trp-Trp-Glu-Leu-Arg and synthetic EGF [Cys(Acm) 20'31] (20–31) Cys-(Acm)-Met-His-Ile-Glu-Ser-Leu-Asp-Ser-Tyr-Thr-Cys(Acm). Epidermal growth factor can be used at a concentration of 0.1 ng/ml–100 mg/ml.

4. Bovine pituitary extract (BPE), an aqueous extract of bovine or human pituitary glands. This growth supplement has been demonstrated mitogenic in vitro to a wide variety of epithelial; i.e., human corneal epithelium, and human epidermal keratinocytes. The Bovine Pituitary Extract can be used at concentrations of: 0.1 ng/ml to 100 mg/ml.

5. Insulin polypeptide hormone that functions in the regulation of cellular carbohydrate metabolism and the synthesis of cellular protein, RNA and neutral lipids. Insulin can be used at concentrations of 0.1 ng/ml to 100 mg/ml.

6. Transferrin used at 0.1 ug/ml–10 mg/ml.

7. Sodium selenite used 0.1 ng/ml–100 mg/ml.

8. Platelet-Derived Growth Factor (PDGF) a polypeptide stored in platelets and released into serum during clotting, has been shown to be a mitogen for cultures fibroblasts cells. Platelet-derived growth factor can be used at 0.1 ng/ml–100 mg/ml.

9. An aqueous extract of bovine or human retinas. This growth supplement has been demonstrated mitogenic in vitro to a wide variety of endothelial cells; i.e., human corneal endothelium and human vascular endothelium. Retinal-derived growth factor can be used at 0.1 ng/ml to 100 mg/ml.

10. Insulin-Like Growth Factor I (IGF-I), a single-chain polypeptide with a molecular weight of 7,650 daltons (76 amino acids and a pI of 8.2 to 8.4). IGF-I, also known as Somatomedin C, is the anabolic basis polypeptide that functions as the mitotic messenger for pituitary growth hormone. Insulin-Like Growth Factor I can be used at 0.1 ng/ml–100 mg/ml.

11. Insulin-Like Growth Factor II (IGF-II) can be used at 0.1 ng/ml–100 mg/ml.

12. Transforming Growth Factor Beta (TGF-$\beta$) has a molecular weight of 25,000 daltons and is a homodimer composed of two identical 112-amino acid chains. TGF- can be used at 0.1 ng/ml–100 mg/ml.

13. Transforming Growth Factor Alpha (TGF-$\alpha$) can be used at 0.1 ng/ml–100 mg/ml.

14. Glycosaminoglycans are used at a concentration of 0.01–10%.
    1. Dermatin sulfate
    2. Heparin sulfate
    3. Heparan sulfate
    4. Keratin sulfate 15. Antioxidants
    1. Ascorbic acid, concentration of 0.001 mM to 100 mM.
    2. Glutathione, concentration of 0.001 mM to 100 mM.
    3. DL-$\alpha$-tocopherol, concentration of 0.001 mM to 100 mM.
    4. 2-mercaptoethanol, concentration of 0.001 mM to 100 mM.

16. Glycoproteins that promote cellular adhesion and migration (wound healing):
    1. Laminin, a large glycoprotein having a molecular weight of approximately 1,000,000 daltons. The laminin molecule has the shape of an asymmetric cross, comprised of 3B chains of 200,000 daltons each, and one A chain of 400,00 daltons. The chains are held together by disulfide bonds. The single A chain contains a binding site for heparin sulfate. The B chains contain type IV collagen binding sites. The intersection of the three B chains is the focus for cell binding. Laminin provides cells with physiological compatible extracellular matrix that will foster attachment, cytoplasmic spreading and proliferation. Laminin can be used at a concentration of 0.1 ng/ml to 100 mg/ml.
    2. Fibronectin is an extracellular matrix associated glycoprotein composed of two disulfidebonded subunits of 220,000 daltons each. Fibronectin has the potential to interact with several cell surface associated macromolecules including collagen, glycosaminoglycans and cell surface receptors. Fibronectin promotes cell adhesion and migration of human corneal endothelial cells, epithelial cells and fibroblasts. Fibronectin can be used at a concentration of 0.1 ng/ml to 100 mg/ml.

17. Extracellular Matrix Components:
    A. A collagen used in the range of 0.1 ng/ml to 1 g/ml selected from the group of:
        1. Type I collagen
        2. Type II collagen
        3. Type III collagen
        4. Type IV collagen
        5. Type V collagen
        6. Type VII collagen
        7. Type VIII collagen; or
    B. Enactin, used at a concentration of 0.1 ng/ml to 100 mg/ml.

18. An energy source in a range of 0.05 mM to 10 mM selected from the group of:
    1. Glucose
    2. Pyruvate
    3. Fructose
    4. Dextrose

MODE OF OPERATION

EXAMPLE 1

A Viscoelastic Solution Containing Chondroitin Sulfate, Hydroxypropyl Methylcellulose, Sodium Hyaluronate and Epidermal Growth Factor This study was conducted to evaluate the in vitro efficacy of Epidermal Growth Factor (EGF) when contained in a chondroitin sulfate, hydroxypropyl methylcellulose, sodium hyaluronate based viscoelastic. The efficacy of the viscoelastic test solutions was determined by measuring the DNA synthesis of human corneal endothelial cells utilizing a $^3$H-thymidine incorporation bioassay.

Isolation techniques developed in our laboratory have enabled the establishment of primary and subsequent subcultures of human corneal endothelium that retain the attributes of native endothelium. In vitro conditions maintain these human corneal endothelial cells in a proliferative state, actively undergoing mitosis. A quantitative bioassay has been developed to determine the effects of various test viscoelastics in the stimulation or inhibition of DNA synthesis as measured by [3H]-thymidine incorporation.

This study examines three aspects of human endothelial cell responses to EGF, including dosage, vehicle and exposure time. 1) Dosage: This study examined the impact of various dosages of EGF, and will be used to evaluate the potential of "down regulation" (a decreased response due to excess EGF) for future in vitro applications. 2) Vehicle: This study also examined the impact of using a chondroitin sulfate, hydroxyprophyl methylcellulose, and sodium hyaluronate based viscoelastic. 3) Exposure Time: This experiment also compared the effect of exposure to EGF over a 24-hour exposure time, stimulating an in vitro condition where the viscoelastic material will be retained in the eye following the surgical procedure

Materials and Methods

A viscoelastic solution containing chondroitin sulfate (0.5%, hydroxypropyl methylcellulose (1.4%), sodium hyaluronate (0.05%) was prepared in a balanced salt solution. The control media was serum free CSM (Chiron Ophthalmics, Inc., Irvine, Calif.), serum free CSM supplemented with 10 ng/ml hEGF and CSM supplemented with 10% fetal bovine serum that was freshly prepared in our own laboratory. A dose response curve was conducted with the viscoelastic containing hEGF at 10 ng/ml, 100 ng/ml and 1 ug/ml. All samples were refrigerated at 4° C. until the time of use, and were then warmed to room temperature at the time of the experiment.

Quantitative Bioassay

The quantitative bioassay is based on the incorporation of [$^3$H]-thymidine into the DNA of human corneal endothelial cells incubated with the test samples, serum free and/or serum containing medium. Costar 96-well tissue culture plates were seeded with $3 \times 10^3$ cells in a final volume of 50 ul of designated medium. Third passage human corneal endothelial cells were maintained in a humidified incubator at 35.5° C. in a 95% air: 5% CO2 atmosphere. After 24 hours of incubation in CSM, supplemented with 10% fetal bovine serum to permit attachment, 100 ul of viscoelastic was applied to each well. After a 24-hour incubation period, each well was rinsed and aspirated with 1 ml of MEM medium. Cells were then incubated with 200 ul of serum free CSM. In control wells, incubation with serum free CSM or CSM supplemented with 10% FBS, each well was also rinsed and aspirated with 1 ml of MEM medium and then incubated with 200 ul of appropriate control medium. In control wells, cells were constantly exposed to defined CSM medium with 10 ng/ml of hEGF. In rinsed control wells, CSM medium with 10 ng/ml was rinsed and aspirated with 1 ml of MEM medium after 24 hours. Human corneal endothelial cells were then incubated for an additional 72 hours in the presence of 1 microcurie/well of [$^3$H]-thymidine. Uptake was ended by the aspiration of the radioactive medium and rinsing the cells twice with serum free Minimal Essential Medium. The human corneal cells were detached with 0.5% trypsin and prepared for liquid scintillation counting. The [$^3$H]-thymidine counts represent acid-insoluble counts. One-way analysis of variance and the Newman-Keuls multiple range test were used to evaluate statistical significance ($p < 0.05$).

Discussion

This study was conducted to evaluate the in vitro efficacy of Epidermal Growth Factor (EGF) when contained in a chondroitin sulfate, hydroxypropyl methylcellulose, sodium hyaluronate based viscoelastic. The efficacy of the viscoelastic test solutions was determined by measuring the DNA synthesis of human corneal endothelial cells utilizing a $^3$H-thymidine incorporation bioassay. This bioassay provides a sensitive method to determine if the test medium will inhibit or stimulate the incorporation of [$^3$H]-thymidine into the DNA of these cells. The incorporation of [$^3$H]-thymidine by human corneal endothelial cells incubated with the viscoelastic test material contained various concentrations of hEGF, was compared to freshly prepared serum free CSM medium and CSM medium supplemented with 10% FBS. One-way analysis of variance and the Newman-Keuls multiple range test were used to evaluate statistical significance ($p < 0.05$).

In this bioassay, the cells were kept in a proliferative state, actively undergoing mitosis. Inhibition of [$^3$H]-thymidine incorporation into the DNA of human corneal endothelial cells is an indicator of decreased cell metabolism, decreased cell health and possible cellular toxicity. This study examined three aspects of human endothelial cell responses to EGF, including dosage, vehicle and exposure time. This study examined the impact of various dosages of hEGF. hEGF concentrations ranged from 10 ng/ml to 1 ug/ml. Viscoelastics containing various concentrations of hEGF were exposed to HCE cells for a 24 hour time. The 24-hour exposure time simulated the in vivo condition where the viscoelastic carrier will be retained in the eye following the surgical procedure. When we compared the [$^3$H]-thymidine incorporation of HCE cells incubated with a viscoelastic containing hEGF versus HCE cells exposed to the control CSM medium and the viscoelastic control, hEGF concentrations of 100 ng/ml and 1 ug/ml exhibited statistically significant differences ($p < 0.05$) as compared to both the medium and viscoelastic control. HCE cells exposed continuously to CSM supplemented with 10 ng/ml hEGF demonstrated a statistically significant increase in [$^3$H]-thymidine incorporation as compared to cells exposed to the CSM control medium.

It should be noted here that growth factors do require time to act. Although they can switch on the transcription of certain genes within minutes, such short stimulations are usually not adequate to induce DNA synthesis. The growth factor must act for several hours, which presumably means that it must be capable of activating the signal pathway for a protracted period. This need for a prolonged stimulus could possibly be the basis for the synergistic interactions that exist between various growth factors. When growth factors combine with cell surface receptors they entrain a sequence of events that gradually commits the cell to enter DNA synthesis. This hypothesis is supported by the fact that as little as 10 ng/ml of hEGF can stimulate statistically significant increases in [$^3$H]-thymidine incorporation when HCE cells are exposed continuously to the growth factor.

In conclusion, this study demonstrates that HCE cells must be exposed to viscoelastics containing growth factors for a prolonged period of time to promote optimum DNA synthesis. Exposure to the viscoelastic containing hEGF concentrations of 100 ng/ml and 1 ug/ml stimulate increased DNA synthesis as compared to viscoelastics without growth factors and will therefore promote greater cell proliferation and greater wound healing.

Various modifications can be made to the present invention without departing from the apparent scope hereof.

We claim:

1. A viscoelastic solution consisting essentially of:
   a. a buffered solution which is at least one of a buffered balanced salt solution (BSS), a HEPES buffered minimum essential medium (MEM), phosphate buffered saline (PBS) or tissue culture medium 199;
   b. at least one of hydroxyprophyl methylcellulose, carboxypropyl methylcellulose, a cellulose gum, dextran or dextran sulfate;
   c. chondroitin sulfate; and,
   d. sodium hyaluronate;

the composition having a pH of 6.0–8.0 and an osmolality of 200–400 mOSmol/L.

* * * * *